United States Patent
Kühling et al.

(10) Patent No.: US 6,316,678 B1
(45) Date of Patent: Nov. 13, 2001

(54) METHOD FOR PRODUCING DIS(4-HYDROXYARYL) ALKANES

(75) Inventors: Steffen Kühling, Sint Niklaas (BE); Rolf Lanze; Rainer Neumann, both of Krefeld (DE); Frieder Heydenreich, Düsseldorf (DE); Tony van Osselaer, Krefeld (DE); Gerhard Fennhoff, Willich (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/786,146
(22) PCT Filed: Aug. 23, 1999
(86) PCT No.: PCT/EP99/06146
 § 371 Date: Feb. 28, 2001
 § 102(e) Date: Feb. 28, 2001
(87) PCT Pub. No.: WO00/14044
 PCT Pub. Date: Mar. 16, 2000

(30) Foreign Application Priority Data
Sep. 3, 1998 (DE) .............................................. 198 40 110

(51) Int. Cl.⁷ ..................................................... C07C 37/68
(52) U.S. Cl. ............................................................. 568/724
(58) Field of Search .............................................. 568/724

(56) References Cited

U.S. PATENT DOCUMENTS

| 2,775,620 | 12/1956 | Williamson | 260/619 |
| 4,859,803 | 8/1989 | Shaw | 568/727 |
| 4,894,486 | 1/1990 | Neil, Jr. et al. | 568/702 |
| 5,059,721 | 10/1991 | Powell et al. | 568/724 |
| 5,288,926 | 2/1994 | Patrascu et al. | 568/727 |
| 5,324,867 | 6/1994 | Asaoka et al. | 568/724 |
| 5,371,304 | 12/1994 | Asaoka et al. | 568/724 |
| 5,382,711 | 1/1995 | Asaoka et al. | 568/722 |
| 5,382,712 | 1/1995 | Asaoka et al. | 568/724 |
| 5,399,789 | 3/1995 | Cipullo et al. | 568/702 |

FOREIGN PATENT DOCUMENTS 0 499 922   8/1992 (EP) .

*Primary Examiner*—Michael L. Shippen
(74) *Attorney, Agent, or Firm*—Joseph C. Gil; Aron Preis

(57) ABSTRACT

The present invention relates to a process for producing bis(4-hydroxy-aryl)alkanes of high purity from addition products of bis(4-hydroxy-aryl)alkanes and aromatic hydroxy compounds which are obtained by the acid-catalysed reaction of the aromatic hydroxy compounds with ketones.

6 Claims, No Drawings

METHOD FOR PRODUCING DIS(4-HYDROXYARYL) ALKANES

The present invention relates to a process for producing bis(4-hydroxy-aryl)alkanes of high purity from addition products of bis(4-hydroxy-aryl)alkanes and aromatic hydroxy compounds which are obtained by the acid-catalysed reaction of the aromatic hydroxy compounds with ketones.

The synthesis of bis(4-hydroxyaryl)alkanes by the acid-catalysed reaction of aromatic hydroxy compounds with ketones is known from U.S. Pat. No. 2,775,620 or EP-A 342 758 for example. As a rule, an addition product of the bis(4-hydroxyaryl)alkane and of the aromatic hydroxy compound which is used as a starting material is obtained as an intermediate, and is subsequently freed from the aromatic hydroxy compound by distillation. The most important example of large-scale industrial production is the production of bisphenol A, during which an addition product of bisphenol A (BPA) and phenol is obtained as an intermediate. Even after purification, by recrystallisation for example, this addition product still contains traces of acid (about 5 to $10.10^{-6}$ mol acid/mol BPA) due to the acid-catalysed production route employed. On the separation of the phenol from bisphenol A, which is associated with an increase in temperature, these traces of acid result in the partial decomposition of the bisphenol and in the formation of by-products. The consequence of these decomposition reactions is an impairment of the purity and quality of colour of the bisphenol. This also has a negative effect on the quality of products produced from the bisphenols, such as epoxy resins, polyesters, polyester carbonates and polycarbonates, the consequences of which are problems of colour, poor transmission of light through transparent products, or pinholes in the surfaces of mouldings produced from these end products. Similar phenomena also occur during the production of other bis(4-hydroxyaryl)alkanes. Improving the thermal stability of bis(4-hydroxyaryl)alkanes and of the addition products thereof with aromatic hydroxy compounds is therefore of particular interest.

Various methods of stabilising bis(4-hydroxyaryl) alkanes have already become known. According to EP-A 374 692, hydroxycarboxylic acids or ammonium or alkali salts thereof are used as additives. According to EP-A 523 931, alkali salts of aliphatic carboxylic acids are added to the relevant addition product of a bis(4-hydroxyaryl)alkane and an aromatic hydroxy compound. U.S. Pat. No. 5,399,789 proposes the addition of amines in amounts of 1 to 1000 ppm to bis(4-hydroxyaryl)alkanes before the thermal work-up of the latter. A common feature of all these processes is that the addition of an excessive amount of basic substances results in the decomposition of the product during thermal work-up and during further thermal processing steps.

EP-A 469 689 describes a process in which the adsorptive effect of activated carbon is utilised in order to protect the bis(4-hydroxyaryl)alkane from cleavage processes in subsequent work-up stages. However, high throughputs of reaction mixture, particularly if the process if operated continuously, result in abrasion of the activated carbon to form very fine particles, even if activated carbon granules are used. These very fine particles can increasingly contaminate the final product and impair the quality of colour and purity thereof, even if very careful filtration is employed.

EP-A 559 372 describes a combination of an acidic and of a basic ion exchange resin which is operated in the form of a mixed bed. The mother liquor is passed through this bed, and is thus purified before it is added to the mixture of starting materials before the actual reaction. However, this process has the disadvantage that substances which promote decomposition and which are first formed in the course of the reaction are not removed and can thus continue to impair the quality of the product. Moreover, oligomers of these resins in dissolved form always enter the product stream and likewise impair the quality of the product.

The object of the present invention was to provide a process by which bis(4-hydroxyaryl)alkanes can be obtained with a reduced proportion of by-products. A process has now been identified in which a neutralising agent is deposited in very finely divided form on the bis(4-hydroxyaryl)alkane addition product. In one preferred embodiment of the process according to the invention, the metered addition of the neutralising agent is controlled depending on the isomer content of the product.

The present invention relates to a process for producing bis(4-hydroxyaryl)-alkanes, wherein an aqueous alkali hydroxide solution, e.g. aqueous NaOH, is fed as an aerosol via the gas phase to an addition product of a bis(4-hydroxyaryl)alkane and the aromatic hydroxy compound which is used as a starting material, which addition product is obtained by the acid-catalysed reaction of aromatic hydroxy compounds with ketones, and the addition product is subsequently freed from the aromatic hydroxy compound by distillation. In a preferred embodiment, the addition product is an addition product of bisphenol A and phenol.

In large-scale industrial processes, the neutralisation of traces of acid which are still present in the addition product due to the production conditions employed is extremely difficult, since only very small amounts of base are necessary and have to be uniformly distributed over the crystalline addition product. According to the present invention, this difficulty is overcome by depositing an aqueous alkali hydroxide solution as an aerosol on the addition product. The amount of alkali hydroxide which is deposited on the addition product is controlled via the concentration of the alkali hydroxide solution which is employed and which is deposited on the addition product. This concentration preferably ranges from 0.005 to 0.015 % by weight alkali hydroxide.

A further difficulty is the control of the neutralisation process, since it has hitherto not been technically possible to perform a pH measurement on the addition product in order to determine the neutral point. In one preferred embodiment of the invention, which is a continuous process for the production of bis(4-hydroxyaryl)alkanes, this problem is solved in that a constant mass flow of alkali hydroxide is fed to the addition product, which occurs in crystalline form and which is freed from mother liquor, the addition product is subsequently freed from the aromatic hydroxy compound which it contains, the content of by-products in the bis(4-hydroxyaryl)alkane obtained is determined by analysis, and if the content of defined by-products exceeds a predetermined threshold value the mass flow of alkali hydroxide is correspondingly readjusted. The content of by-products in the bis(4-hydroxyaryl)alkane obtained is preferably determined by gas chromatography or by high-pressure liquid chromatography. Determination of the by-products can also be effected on-line. The interval between control operations can thereby be shortened and variations in product composition can be minimised. The alkali hydroxide is preferably supplied as an aerosol of an aqueous alkali hydroxide solution and the mass flow of alkali hydroxide is controlled via the concentration of the alkali hydroxide solution. In one particularly preferred embodiment, dilute alkali hydroxide solution is used as the operating liquid of a water ring pump and an aerosol is thereby produced on the delivery side. The alkali hydroxide concentration in the aerosol can be controlled by a continuous, quantitatively controlled feed of water and alkali hydroxide solution and by the continuous removal of part of the operating liquid. In addition, the pump acts as a mixing unit and ensures homogeneous mixing throughout of the operating liquid.

The process according to the invention is suitable for producing bis(4-hydroxyaryl)alkanes which are based on ketones which comprise at least one aliphatic group on their carbonyl function. Examples thereof include acetone, methyl ethyl ketone, methyl propyl ketone, methyl isopropyl ketone, diethyl ketone, acetophenone, cyclohexanone, cyclopentanone, and methyl-, dimethyl- and trimethylcyclohexanones which may also contain geminal methyl groups, e.g. 3,3-di-methyl-5-methylcyclohexanone (hydroisophorone). Acetone, acetophenone, cyclohexanone and homologues thereof which contain methyl groups are preferred; acetone is particularly preferred.

Aromatic compounds which are suitable for producing addition products of a bis(4-hydroxy-aryl)alkane and an aromatic hydroxy compound which are used in the process according to the invention are not substituted in the p-position and contain no second order substituents such as cyano, carboxy or nitro groups; examples thereof include phenol, o- and m-cresol, 2,6-dimethylphenol, o-tert.-butyl phenol, 2-methyl-6-tert-butylphenol, o-cyclohexylphenol, o-phenylphenol, o-isopropylphenol, 2-methyl-6-cyclopentyl-phenol, o- and m-chlorophenol, and 2,3,6-trimethylphenol. Phenol, o- and m-cresol, 2,6-dimethylphenol, o-tert.-butylphenol and o-phenyl-phenol are preferred; phenol is particularly preferred.

EXAMPLES

Example 1

A crystalline addition product of bisphenol A and phenol was obtained by the acid catalysed reaction of phenol and acetone in a continuous process, and was separated from the mother liquor by filtration. The amount of NaOH which was necessary for neutralisation was continuously fed as an aerosol via the gas phase to the crystallised BPA/phenol addition product. The amount of NaOH which was deposited on the BPA/phenol addition product was controlled via the concentration of the aqueous NaOH solution employed; this concentration ranged from 0.005 to 0.015 % by weight NaOH. The concentration was quantitatively controlled by diluting an 6.5 % by weight NaOH solution with deionised water. The BPA which resulted after the thermal separation of the phenol was analysed by gas chromatography at intervals of 4 hours. The NaOH concentration was controlled depending on the content of isomers in the BPA. If the total content of isopropenylphenol and dimers thereof was less than 100 ppm, the concentration of the NaOH was left unchanged. At higher contents, the NaOH concentration was increased. At dimer concentrations <10 ppm and at increased contents of bisphenol (>300 ppm), which indicated basic decomposition, the NaOH concentration was reduced. Using this procedure, the contents of dimers and of isopropenylphenols in the bisphenol produced could be limited to values <100 ppm. A higher grade of BPA, which was significantly more constant, could be achieved by the continuous metered addition of NaOH, which was controlled by GC analysis (of the contents of dimers, isopropenylphenol and trisphenol).

Comparative Example 2

No NaOH was fed via the gas phase to the crystallised BPA/phenol addition product. The total content of isopropenylphenol and dimers thereof in the BPA increased to 900 ppm. A high grade of BPA with a low content of isomers (dimers, isopropenylphenol and trisphenol) was not achieved.

Comparative Example 3

An amount of NaOH which corresponded to the amount of NaOH which was supplied over a period of 24 hours in Example 1 was added discontinuously every 24 hours via the gas phase to the crystallised BPA/phenol addition product. As a result, it was observed that the content of isopropenylphenol, of dimers thereof and of trisphenol in the BPA varied considerably. The content of dimers and of isopropenylphenol fluctuated between <100 and 700 ppm, and the content of trisphenols fluctuated between 250 and 500 ppm. A constant grade of BPA with a low content of isomers was not obtained.

What is claimed is:

1. A process for producing bis(4-hydroxyaryl)alkanes from addition products of bis(4-hydroxyaryl)alkanes and aromatic hydroxy compounds which are obtained by the acid-catalysed reaction of the aromatic hydroxy compounds with ketones, wherein an aqueous alkaline solution is fed as an aerosol via the gas phase to the crystalline addition product and the addition product is subsequently freed from the aromatic hydroxy compound by distillation.

2. The process of claim 1, wherein the addition product of a bis(4-hydroxyaryl)alkane and an aromatic hydroxy compound is an addition product of bisphenol A and phenol.

3. The process of claim 2, wherein 0.005 to 0.015% by weight aqueous NaOH is used as the aqueous alkali hydroxide solution.

4. The process of claim 1, wherein during the continuous production of bis(4-hydroxyaryl)alkanes a constant mass flow of alkali hydroxide is fed to the addition product, which occurs in crystalline form and which is freed from mother liquor, the addition product is subsequently freed by distillation from the aromatic hydroxy compound which it contains, the content of by-products in the bis(4-hydroxyaryl)alkane obtained is determined by analysis, and if the content of defined by-products exceeds a predetermined threshold value the mass flow of alkali hydroxide is correspondingly readjusted.

5. The process of claim 1, wherein the aerosol is produced on the delivery side of a water ring pump which is operated using dilute alkali hydroxide solution as the operating liquid.

6. A process according to claim 5, wherein the alkali hydroxide concentration in the aerosol is controlled by a continuous, quantitatively controlled feed of water and alkali hydroxide solution and by the continuous removal of part of the operating liquid.

* * * * *